United States Patent [19]

Davies

[11] 4,255,332
[45] Mar. 10, 1981

[54] PROCESS FOR THE PREPARATION OF POTASSIUM CLAVULANATE FROM LITHIUM CLAVULANATE

[75] Inventor: Richard V. Davies, Worthing, England

[73] Assignee: Beecham Group Limited, England

[21] Appl. No.: 935,887

[22] Filed: Aug. 23, 1978

[30] Foreign Application Priority Data

Sep. 1, 1977 [GB] United Kingdom ............... 36567/77

[51] Int. Cl.$^3$ .......................................... C07D 498/04
[52] U.S. Cl. .................................................. 260/245.3
[58] Field of Search ...................................... 260/245.3

[56] References Cited

U.S. PATENT DOCUMENTS 4,144,242   3/1979   Fleming et al. .................... 260/245.3

OTHER PUBLICATIONS

"Handbook of Chemistry & Physics", p. B189, 48th Edition (Chemical Rubber Co.).

Primary Examiner—Mark L. Berch
Attorney, Agent, or Firm—Jacobs & Jacobs

[57] ABSTRACT

The present invention provides a process for the preparation of potassium clavulanate which process comprises contacting a concentrated solution of lithium clavulanate with a concentrated solution of potassium fluoride, potassium orthophosphate, potassium metaphosphate potassium carbonate or potassium bicarbonate, separating off the resulting precipitated lithium fluoride, lithium orthophosphate, lithium metaphosphate or lithium carbonate and thereafter recovering the potassium clavulanate from solution.

15 Claims, No Drawings

PROCESS FOR THE PREPARATION OF POTASSIUM CLAVULANATE FROM LITHIUM CLAVULANATE

The present invention relates to a process for the preparation of potassium calvulanate.

Belgian Pat. No. 827,926 discloses inter alia potassium calvulanate of the formula (I):

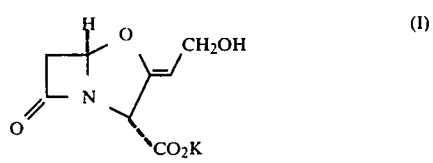

and the process for its preparation by isolation from the fermentation liquor of *Streptomyces clavuligerus*. German Offenlegungsschrift No. 2604697 subsequently disclosed the preparation of potassium calvulanate from lithium clavulanate via the ion-exchange resin Dowex 50 W. The Offenlegungsschrift also pointed out that lithium ions have a 'surprisingly high affinity' for clavulanate ions so that lithium clavulanate may be precipitated out from solutions containing other ions. It is therefore unexpected that potassium clavulanate may be readily prepared from lithium clavulanate by precipitating out a lithium salt in a manner which leaves the potassium clavulanate in solution from which it can be recovered thereafter in pure form.

A process for the preparation of potassium clavulanate from lithium clavulanate has now been discovered that beneficially avoids the use of expensive ion exchange resins and yet provides a good yield of a pure product.

The present invention provides a process for the preparation of potassium clavulanate which process comprises contacting a concentrated solution of lithium clavulanate with a concentrated solution of potassium fluoride, potassium orthophosphate, potassium metaphosphate, potassium carbonate or potassium bicarbonate, separating off the resulting precipitated lithium fluoride, lithium orthophosphate, lithium metaphosphate or lithium carbonate and thereafter recovering the potassium clavulanate from solution.

Aptly the potassium salt is potassium fluoride, potassium orthophosphate or potassium carbonate.

The solutions to be mixed will contain essentially 1 equivalent of lithium ion per equivalent of potassium ion. No major excess (for example not more than 5%) of lithium ion should be present or the purity of the final product will be undesirably reduced. An excess of potassium ion may be employed, for example 1–2 and more suitably 1.2–1.5 equivalents.

The solutions used in this process will be concentrated, that is to say they will preferably be saturated solutions or substantially saturated solutions, for example solutions which are at least 80% saturated (a 11% w/v solution of lithium clavulanate in water represents an approximate saturation at room temperature).

The solvent or solvents employed may be water or water in admixture with miscible organic solvents such as acetone or a $C_{1-4}$ alkanol such as methanol, ethanol or isopropanol. Aptly, the solvent or solvents employed may be water or water in admixture with acetone.

The solvent mixture will not contain high proportions of organic solvents which would precipitate the potassium salts. In general the organic component should be present in the initial lithium clavulanate solution or may be added after the contacting of the lithium clavulanate and potassium salt solution.

It has been found that water/acetone mixtures are particularly suitable since they give rise to good yields of material of acceptable purity. In general the initial lithium clavulanate solution may contain up to 45% v/v of acetone, for example 10 to 40% v/v of acetone (but eventually may contain up to 92% v/v acetone before finally separating off the insoluble inorganic lithium salts). Such solutions may also contain a lower alkanol if desired, for example about 10–40% v/v.

The precipitated lithium salt is most readily separated from the solution of the potassium clavulanate by filtration.

It has proved convenient to recover the potassium clavulanate from the filtrate (after separation of the lithium salt) by precipitation, for example by adding a sufficient amount of a miscible organic solvent such as acetone. Alternatively (and less preferably) the potassium salt may be obtained by removing the solvent, for example by evaporation at low pressure. The desired salt will generally be obtained in crystalline form by either of these processes. This may be encouraged in conventional manner, for example by trituration under acetone or by seeding the concentrated solution or the like.

A potassium salt favoured in the process of this invention comprises a potassium orthophosphate. Most suitably the potassium orthophosphate used does not contain any impurities such as potassium hydroxide which cause the pH of the medium to reach values greater than 10 in molar solution. It has been found that potassium orthophosphate prepared by neutralisation of phosphoric acid with potassium carbonate is more suitable than commercial potassium orthophosphate prepared by neutralisation of phosphoric acid with potassium hydroxide. Most suitably the potassium orthophosphate is added in such a manner that the pH does not rise about 9.5 and more suitably not above 9.2, for example not above 8.2.

Tripotassium orthophosphate is most suitably employed in this form of the process of the invention but dipotassium phosphate or dipotassium phosphate and potassium carbonate may also be used.

A further particularly favoured salt for use is potassium fluoride.

It is generally favourable to prepare a solution of lithium clavulanate and to add to this just sufficient of the organic solvent to precipitate any impurities from the lithium clavulanate present without precipitating the potassium clavulanate. The solution may then be filtered and the filtrate treated with the potassium salt solution. The potassium clavulanate may be precipitated from the resulting solution by dilution with acetone or other miscible organic solvent.

The ratio of organic solvent to water used at the precipitation of impurities is often about 7:1 to 14:1, for example about 9:1 or about 12:1. The ratio of organic solvent to water at the precipitation of potassium clavulanate is often about 30:1 to 45:1, for example about 32:1 or about 41:1.

The purity of the lithium clavulanate used in this process is preferably at least 50% w/w in order to achieve acceptable recoveries although lower purities (for example 35% w/w) may be employed less advantageously. In general recoveries improve if the purity of the starting material improves, thus it is more suitable to employ lithium clavulanate of at least 60% w/w purity, yet more suitably of at least 80% purity, preferably of at least 90% purity and particularly advantageously of at least 95% purity.

EXAMPLE 1

Lithium clavulanate (20.6 g; 0.1 mole; estimated purity 95% expressed as pure free acid) was dissolved in the minimum volume of water (170 ml) at room temperature, acetone (40 ml) added and the solution cooled in an ice bath. Tri-potassium orthophosphate solution (33.6 ml of 1 M solution) was added with stirring at a rate such that the pH did not rise above 8.2. The rate of addition was slow at first but, on seeding with a small quantity of lithium orthophosphate and commencement of precipitation, the addition rate was increased. When addition was complete the pH was 7.6. A further portion (40 ml) of acetone and potassium phosphate solution (2 ml) were added to ensure complete precipitation of lithium phosphate. At this point the pH rose to 8.1. After 5 minutes the pH was reduced to 7.6 by the addition of dilute orthophosphoric acid. The resulting solution was then made up to 1.8 liters with acetone, allowed to stand for 10 minutes and then filtered through celite. The filtrate was added to 30 volumes of acetone (5.4 liters) slowly with stirring. After about ½ hour after the last addition the precipitate was filtered off and washed with acetone (3×200 ml). The resulting material was kept in a vacuum oven at room temperature overnight to give a white solid (18.5 g). (This material assayed to 82.6% pure expressed as pure free acid and contained less than 0.05% phosphate and 0.1% lithium.)

EXAMPLE 2

Lithium clavulanate (10.3 g; 0.05 mole) in water (90 ml) was cooled in an ice bath. Potassium fluoride solution (4.7 g KF.2H$_2$O; 0.05 mole in 10 ml water) was added slowly over 20 minutes. Precipitation of lithium fluoride commenced almost immediately. When addition was complete about 5 volumes of acetone (500 ml) was added over ½ hour. After a further ¼ hour the mixture was filtered to yield lithium fluoride (1.25 g).

The filtrate was made up to 10 volumes (1 liter) with acetone and filtered through celite (3 g). The filtrate was added to 30 volumes of acetone (3 liters) with stirring over ¾ hour. The mixture was filtered after a further ¼ hour and the solid washed with acetone. The solid was dried at ambient temperature under vacuum and yielded potassium clavulanate (9.6 g).

(This material assayed as 84.0% pure expressed as pure free acid and contained less than 0.1% fluoride and less than 0.002% lithium.)

EXAMPLE 3

Lithium clavulanate (10.3 g; 0.05 mole) was dissolved in water (90 ml) and cooled in an ice bath. Acetone (60 ml) was then added. A solution of potassium carbonate (3.5 g; 0.025 mole in 10 water) was added slowly to the clavulanate solution. The first 3 drops caused the pH to reach 10.3. A few milligrams of lithium carbonate solid were added to seed out the lithium carbonate formed during the reaction. At this point the pH started to decrease. The remaining potassium carbonate solution was then added at a rate such that the pH remained about 10. Halfway through this addition a small volume of acetone (30 ml) was added. After a further ¼ hour the mixture was made up slowly to 650 ml) with acetone. The lithium carbonate was then filtered off. (Weight obtained 1.95 g.) The filtrate was made up to 1 liter with acetone and filtered through celite (3 g) thereby removing most of the yellow colour which had formed. The resulting liquor was slowly added to 30 volumes acetone (3 liters) over ¾ hour, left 1 hour and then filtered. The resulting solid washed with acetone and dried under vacuum at room temperature to give potassium clavulanate (very slight yellow tint) (8.5 g). (This material assayed as 81.5% pure expressed as pure free acid and contained 0.22% lithium.)

EXAMPLE 4

Lithium clavulanate (21.9 g, estimated purity 67% as pure free acid, 3/40 mole) was stirred in distilled water (135 mls) and isopropanol added (108 mls) with stirring and cooling in an ice bath. The supernatant liquid was decanted off the gummy precipitate (6.0 gm) and a solution (37.8 mls 1.5 eq) of 1 M potassium orthophosphate added slowly with about 20 mg lithium phosphate for seeding. As lithium phosphate separated the pH changed from 8.2 to 7.1 ending up at 7.65 on total addition. The mixture was made up to 500 mls with acetone and filtered and the clear yellow filtrate was divided into 3 equal portions. Portion 1 was made up to 600 mls with acetone, filtered via celite (2 gm) and added to 2.4 liters acetone slowly with stirring. The white solid was filtered off, washed with acetone and fluid bed dried to give potassium clavulanate (4.94 g, 82.1% pfa, 83% recovery). Portion 2 was made up to 800 mls, filtered as above and added to 2.2 l acetone. The solid was filtered off and dried to give potassium clavulanate (4.88 g, 81.9% pfa, 82% recovery). Portion 3 was made up to 1000 mls, filtered as above and added to 2 l acetone. The solid was filtered off and dried to give potassium clavulanate (4.84 g, 82.3 pfa, 82% recovery).

In place of isopropanol in the above Example ethanol or industrial methylated spirits may be used. Addition of an alkanol in this manner is advantageous when employing relatively impure lithium clavulanate possibly due to early precipitation of the impurities.

EXAMPLE 5

Lithium clavulanate (5.15 g, estimated purity 95% pfa, 0.025 moles) was dissolved in 45 mls water and cooled in an ice bath. Tripotassium orthophosphate (10.1 mls of 1 M solution; 1.2 equivs) was added in one lot. The solution was seeded with lithium orthophosphate (1 mg) and acetone (20 ml) added over ½ hr. By this time a large quantity of lithium phosphate had separated out and the pH dropped from 8.3 to 7.4. The solution was made up to 100 ml with acetone over 20 minutes and was then made up to 800 mls with acetone over a further 10 minutes. The mixture was stirred with celite (2 gms) and filtered. The clear filtrate was added to acetone (1750 mls) over 1 hr. The white solid was filtered off and washed with acetone (3×50 ml) (being careful not to pull dry on the filter), and dried on a fluid bed dryer to yield potassium clavulanate (5 g, 83.0% pfa, 85% recovery).

EXAMPLE 6

Lithium clavulanate (5.15 g, estimated purity 95% pfa; 0.025 moles) was dissolved in water (45 mls) and cooled in an ice bath. Tripotassium orthophosphate (10.1 mls of 1 M solution; 1.2 equivalents) was added in one lot. Ethanol (32 mls) was added slowly over ½ hour by which time lithium phosphate had precipitated out and the pH had fallen from 8.3 to 7.3. The mixture was then made up to 800 mls with acetone over ¾ hr. Celite (2 gm) was added and then the mixture was filtered to give a clear, colourless filtrate. This was added with rapid stirring to acetone (1750 mls) over 1 hr and the white solid was filtered off, washed with acetone (3×50 mls) and dried on a fluid bed dryer to yield potassium clavulanate (4.8 g, 82.9 pfa, 81% recovery).

EXAMPLE 7

Lithium clavulanate (5.15 g, estimated purity 95% pfa; 0.025 moles) was dissolved in water (45 mls) and cooled in an ice bath. Potassium fluoride solution (2.82 g KF.2H$_2$O, 1.2 eq in 7 ml water) was added over 15 mins. Lithium fluoride started to separate out after less than 1 ml had been added. Isopropanol (32 mls) was added over ½ hr and the mixture made up to 600 ml with acetone over 8 hr. The mixture was stirred with celite (2 gm) and filtered to give a clear, colourless solution. This was added with rapid stirring to acetone (1400 mls) over 1 hr and the white solid filtered off, washing with acetone (3×500 ml) and dried on a fluid bed dryer to yield potassium clavulanate (4.8 g, 82.9% pfa, 81% recovery).

EXAMPLE 8

Lithium clavulanate (5.6 gm, estimated purity 88.8% pfa 0.025 M) was dissolved in water (45 mls) and the resulting pale-red-brown solution was cooled in an ice bath. Tripotassium orthophosphate (10.1 mls of 1 M solution, 1.2 equivalents) was added in one lot and methanol (18 mls) added over ½ hr with a small quantity of lithium phosphate (ca. 1 mg) for seeding. As lithium phosphate separated out the pH dropped from 8.7 to about 7.5. Acetone was added over ¾ hr to 800 mls. The material that separated out was quite orange-brown at this point and the supernatant a very pale yellow. Celite (2 g) filtration gave a clear solution which was added to acetone (1750 mls) with vigorous stirring over 1 hr. The white solid was filtered off leaving a very pale yellow filtrate. Washing with acetone (3×50 ml) and fluid bed drying gave potassium clavulanate (4.1 g, 84% pfa, 69% recovery).

EXAMPLE 9

Lithium clavulanate (7.15 g, estimated purity 68% pfa; 0.025 M) was stirred in water (45 mls) and about 200 mg insoluble material filtered off. The filtrate (dark brown) was chilled in an ice bath and the potassium phosphate (10.1 mls of 1 M solution; 1.2 equivalents) added in one lot. Isopropanol (32 mls) was added over ½ hr by which time some gummy material separated out. The mixture was made up to 100 ml with acetone over ¼ hr and transferred to another vessel leaving behind a pale gummy deposit. The decanted liquor was then made up to 800 ml with acetone causing the precipitation of highly coloured (brown) gummy material which was separated off via filtration with celite (4 gm). The clear pale yellow solution was then added to acetone (1750 ml) over 1 hr, stirring vigorously and the mixture was then filtered to afford a pale yellow solid which was washed with acetone (3×50 ml) and dried on a fluid bed dryer to yield potassium clavulanate (2 g, 81.2% pfa, 33% recovery).

EXAMPLE 10

Lithium clavulanate (7.15 g, estimated purity 68% pfa 0.025 moles) was stirred in water (45 mls) and cooled in ice. Potassium fluoride solution (3.5 g KF.2H$_2$O in 9 mls solution; 1.5 equivalents) was added slowly to the cloudy brown solution and lithium fluoride separated out as a fairly gummy deposit. The mixture was made up to 100 ml with acetone over ¾hr and then up to 800 mls with acetone over ½ hr. The solid which had separated now was dark brown and was removed by filtration through celite (4 gm). The almost colourless filtrate was added to acetone (1750 ml) over 1 hr with rapid agitation, then filtered and washed with acetone (3×50 ml) and fluid bed dried to give a fine granular just off-white solid potassium clavulanate (3.6 g, 83.1% pfa, 62% recovery).

EXAMPLE 11

To a 10% solution of lithium clavulanate (ca. 95% pure) (0.025 moles in 45 ml water) was added a solution of a potassium salt (1.2 equivalents). The concentration of clavulanate had been reduced to about 8% at the end of this addition. At this point 18 ml of methanol, 32 ml ethanol or 36 ml isopropanol were optionally added. This solution was treated by method (a) or (b) as follows:

Method (a)

The solution was made up to 600 mls with acetone (to give a 9:1 organic:water mixture), the solution was filtered and the filtrate added to 1400 ml of acetone (to give a 32:1 organic:water mixture). The resulting precipitate of potassium clavulanate was filtered off and dried.

Method (b)

The solution was made up to 800 ml with acetone (to give a 12:1 organic:water mixture), the solution was filtered and the filtrate added to 1750 ml of acetone (to give a 41:1 organic:water mixture). The resulting precipitate of potassium clavulanate was filtered off and dried.

The results obtained were as follows:

| Substrate 1.2. Equivalents | Methanol/ Acetone % Yield | Methanol/ Acetone % pfa | Ethanol/ Acetone % Yield | Ethanol/ Acetone % pfa | Iso- propanol/ Acetone % Yield | Iso- propanol/ Acetone % pfa | Acetone/ Acetone % Yield | Acetone/ Acetone % pfa | Method |
| --- | --- | --- | --- | --- | --- | --- | --- | --- | --- |
| K$_3$PO$_4$ | 65 | 80.0 | 68 | 82.5 | 76 | 83.0 | 74 | 80.0 | a |
| K$_3$PO$_4$ | 75 | 80.3 | 81 | 82.9 | 81 | 83.4 | 72 | 83.5 | b |
| KF | 68 | 78.4 | 73 | 81.3 | 77 | 83.6 | 62 | 79.8 | a |
| KF | 73 | 83.2 | 78 | 82.7 | 71 | 82.9 | 57 | 84.6 | b |

EXAMPLE 12

The method of Example 11 was employed but 1.2, 1.5 or 2.0 equivalents of potassium salt were variously used.

No alcohols were added. The results obtained were as follows:

| Substrate | 1.2 equivs. | | 1.5 equivs. | | 2.0 equivs. | | Method |
| --- | --- | --- | --- | --- | --- | --- | --- |
| | % Yield | % pfa | % Yield | % pfa | % Yield | % pfa | |
| $K_3PO_4$ | 76 | 83.0 | 75 | 83.2 | 67 | 83.6 | a |
| $K_3PO_4$ | 85 | 83.0 | 82 | 83.6 | 74 | 81.8 | b |
| KF | 64 | 84.0 | 59 | 82.8 | 49 | 82.2 | a |
| KF | 59 | 82.2 | 52 | 82.6 | 50 | 81.1 | b |

I claim:

1. A process for the preparation of potassium clavulanate which process comprises contacting a concentrated solution of lithium clavulanate in water or in water in admixture with one or more suitable miscible organic solvents with a concentrated solution of potassium fluoride, potassium orthophosphate, potassium metaphosphate, potassium carbonate or potassium bicarbonate, separating off the resulting precipitated lithium fluoride, lithium orthophosphate, lithium metaphosphate or lithium carbonate and thereafter recovering the potassium clavulanate from solution.

2. A process according to claim 1 which employs potassium orthophosphate.

3. A process according to claim 2 which employs tripotassium orthophosphate.

4. A process according to claim 1 which employs potassium fluoride.

5. A process according to claim 1 wherein the solvent of the solution from which the inorganic lithium salt is precipitated is a water/acetone mixture.

6. A process according to claim 1 wherein the solvent also contains a lower alkanol.

7. A process according to claim 1 which employs 1-2 equivalents of potassium ion per equivalent of lithium ion.

8. A process according to claim 7 which employs 1.2-1.5 equivalents of potassium ion per equivalent of lithium ion.

9. A process according to claim 1 solution by precipitation brought about by dilution with acetone and thereafter filtering off the potassium clavulanate.

10. A process according to claim 1 wherein the lithium clavulanate employed is at least 60% w/w pure.

11. A process according to claim 10 wherein the lithium clavulanate employed is at least 90% w/w pure.

12. A process according to claim 11 wherein the lithium clavulanate employed is at least 95% w/w pure.

13. A process according to claim 5 wherein the initial lithium clavulanate solution contains up to 45% v/v of acetone.

14. A process according to claim 13 wherein the solution contains 10–40% v/v of acetone.

15. A process according to claim 6 where the solvent contains 10–40% v/v of a lower alkanol.

* * * * *